(12) United States Patent
Yang et al.

(10) Patent No.: US 9,671,320 B2
(45) Date of Patent: Jun. 6, 2017

(54) SEMI-DRY TYPE ELECTROSTATIC CYCLONE SAMPLER AND METHOD FOR SAMPLING GAS AND/OR WATER SAMPLE

(71) Applicant: JUSUN INSTRUMENTS CO., LTD., New Taipei (TW)

(72) Inventors: Jonathan Yang, New Taipei (TW); Chuen-Jinn Tsai, New Taipei (TW)

(73) Assignee: Jusun Instruments Co., Ltd., New Taipei (TW)

( * ) Notice: Subject to any disclaimer, the term of this patent is extended or adjusted under 35 U.S.C. 154(b) by 68 days.

(21) Appl. No.: 14/831,574

(22) Filed: Aug. 20, 2015

(65) Prior Publication Data

US 2017/0052094 A1 Feb. 23, 2017

(51) Int. Cl.
*G01N 1/22* (2006.01)
*G01N 1/38* (2006.01)

(52) U.S. Cl.
CPC .............. *G01N 1/2202* (2013.01); *G01N 1/38* (2013.01)

(58) Field of Classification Search
CPC ...... G01N 1/2211; G01N 1/2202; G01N 1/22; G01N 1/38
USPC ..................................................... 73/863.21
See application file for complete search history.

(56) References Cited

U.S. PATENT DOCUMENTS

| | | | | |
|---|---|---|---|---|
| 5,914,454 A * | 6/1999 | Imbaro | ............. | B01D 53/1418 261/79.2 |
| 6,484,594 B1 * | 11/2002 | Saaski | ................. | G01N 1/2273 73/863.21 |
| 6,532,835 B1 * | 3/2003 | Saaski | ................. | G01N 1/2273 73/863.21 |
| 6,955,075 B2 * | 10/2005 | Carlson | ..................... | B03C 3/32 73/28.02 |
| 7,472,612 B2 * | 1/2009 | Zaromb | ............... | G01N 1/2214 73/31.01 |
| 7,767,150 B1 * | 8/2010 | Zaromb | ............... | G01N 1/2202 422/400 |
| 2002/0018211 A1 * | 2/2002 | Megerle | ................. | G01N 15/14 356/440 |
| 2004/0069047 A1 * | 4/2004 | Coyle | ................. | B01D 50/004 73/28.04 |
| 2006/0016728 A1 * | 1/2006 | Shorts | .................... | B01D 45/12 209/1 |

(Continued)

*Primary Examiner* — Lisa Caputo
*Assistant Examiner* — Philip Cotey
(74) *Attorney, Agent, or Firm* — Muncy, Geissler, Olds & Lowe, P.C.

(57) ABSTRACT

A semi-dry type electrostatic cyclone sampler includes a cyclone body, an insulate element, a discharge electrode, an air tube, an air introducing means, a discharging means and a flushing means. The insulate element is disposed at a top of the cyclone body and co-defines a cyclone chamber with the cyclone body. The discharging electrode is disposed on the insulate element. The air tube is disposed at a bottom of the cyclone body. The air introducing means is for introducing a particulate-containing air stream into the cyclone chamber. The discharging means is for charging the particulates so that the particulates can attach to an inside of the cyclone body. The flushing means is for flushing the inside of the cyclone body and collecting part of the particulates. When the discharging means activates, the air introducing means activates simultaneously. When the flushing means activates, the discharging means is deactivated.

10 Claims, 10 Drawing Sheets

(56) References Cited

U.S. PATENT DOCUMENTS

| | | | | |
|---|---|---|---|---|
| 2006/0123752 A1* | 6/2006 | Symonds | ............... | B01D 45/16 55/434.2 |
| 2007/0113685 A1* | 5/2007 | Zaromb | ............... | G01N 1/2214 73/863.21 |
| 2009/0151565 A1* | 6/2009 | Tressler | ................ | B01D 47/05 95/187 |
| 2012/0174650 A1* | 7/2012 | Ariessohn | ................ | B08B 3/12 73/23.2 |
| 2014/0020558 A1* | 1/2014 | Gururaja Rao | ........ | B01D 45/12 95/69 |
| 2014/0151543 A1* | 6/2014 | Nagano | ................ | G01N 1/2214 250/282 |
| 2014/0238106 A1* | 8/2014 | Kashima | ............. | G01N 1/2202 73/23.2 |
| 2014/0339415 A1* | 11/2014 | Caldow | ................ | G01N 27/624 250/281 |
| 2015/0233796 A1* | 8/2015 | Kashima | ............. | H01J 49/0422 250/288 |

* cited by examiner ture only, and thus are not imitative of the present invention, and wherein:

SEMI-DRY TYPE ELECTROSTATIC CYCLONE SAMPLER AND METHOD FOR SAMPLING GAS AND/OR WATER SAMPLE

BACKGROUND OF THE INVENTION

1. Field of the Invention

The present invention relates generally to a sampler and its sampling method, and more particularly to a semi-thy type electrostatic cyclone sampler and its method for sampling gas and/or water sample.

2. Description of the Related Art

Air that people breathes everyday comprises multiple chemicals which probably have contaminates harming people's health and the environment. When the concentration of the contaminates is too high, the contaminates might endanger people and environment.

In order to evaluate the risk people or environment exposing to the air pollution, the development of an effective sampler and sampling method is essential. Because contaminates may be gas or solid suspensions, further consideration is needed to sample gas and solid suspensions individually in order to analyze the contaminates more accuracy.

SUMMARY OF THE INVENTION

The present invention has been accomplished in view of the above-noted circumstances. It is an objective of the present invention to provide a sampler and a method which can sample gas and solid suspensions individually.

To achieve the above and other objectives, the present invention provides a semi-dry type electrostatic cyclone sampler comprising a cyclone body, an insulate element, at least one discharge electrode, an air tube, an air introducing means, a discharging means, and a flushing means. The cyclone body has an annular wall, a base connecting to a bottom end of the annular wall, at least one gas inlet, and at least one water outlet. The insulate element is disposed at a top end of the annular wall and co-defines a cyclone chamber with the annular wall and the base of the cyclone body. The gas inlet and the water outlet both communicate with the cyclone chamber. The at least one discharge electrode is disposed on the insulate element and extends into the cyclone chamber. The discharge electrode has a distal end lower than the gas inlet and higher than the water outlet. The air tube is disposed at the base of the cyclone body and defines a passage. A top end of the air tube is defined as a top opening, which communicates the cyclone chamber with the passage. The top end of the air tube is lower than the distal end of the discharge electrode and higher than the water outlet. The air introducing means is for introducing a particulate-containing air stream into the cyclone chamber through the gas inlet in a way that the air stream spirally flows along the annular wall and is expelled from the cyclone chamber via the passage. The discharging means is for applying a high voltage power to the discharge electrode to electrically charge at least a part of the particulates in a way that the charged particulates can attach on the annular wall. The flushing means is for introducing water into the cyclone chamber to flush the annular wall, collect at least a part of the particulates attached on the annular wall and thus form a particulates-containing water sample. The water outlet is adapted for the particulate-containing water sample to leave the cyclone chamber. When the discharging means is activated, the air introducing means is activated simultaneously. When the flushing means is activated, the discharging means is deactivated.

It is another objective of the present invention to provide a gas and water sampling method.

To achieve the above and other objectives, the present invention provides a gas and water sampling method using the aforementioned semi-dry type electrostatic cyclone sampler including the following steps: (1) activating the air introducing means and the discharging means simultaneously, collecting and analyzing the air sample leaving the passage, (2) deactivating the air introducing means and the discharging means, and (3) activating the flushing means, collecting and analyzing the particulate-containing water sample leaving the water outlet.

It is still another objective of the present invention to provide a water sampling method.

To achieve the above and other objectives, the present invention provides a water sampling method using the aforementioned semi-dry type electrostatic cyclone sampler including the following steps: (1) activating the air introducing means and the discharging means simultaneously, (2) deactivating the air introducing means and the discharging means, and (3) activating the flushing means, collecting and analyzing the particulate-containing water sample leaving the water outlet.

As a result, when the air introducing means and the discharging mean are activated, solid suspensions or droplets (both refers to particulates) are collected on the annular wall due to the effects of inertia or electrostatic. The water introduced by the flushing means collects the particulates away from the annular wall. The water containing the aforementioned particulates and expelled from the water outlet and is adapted for subsequent analysis. Hence, the objective of individually sampling gas and/or water samples is achieved.

BRIEF DESCRIPTION OF THE DRAWINGS

The present invention will become more fully understood from the detailed description given herein below and the accompanying drawings which are given by way of illustration only, and thus are not imitative of the present invention, and wherein.

DETAILED DESCRIPTION OF THE INVENTION

Figure 1:
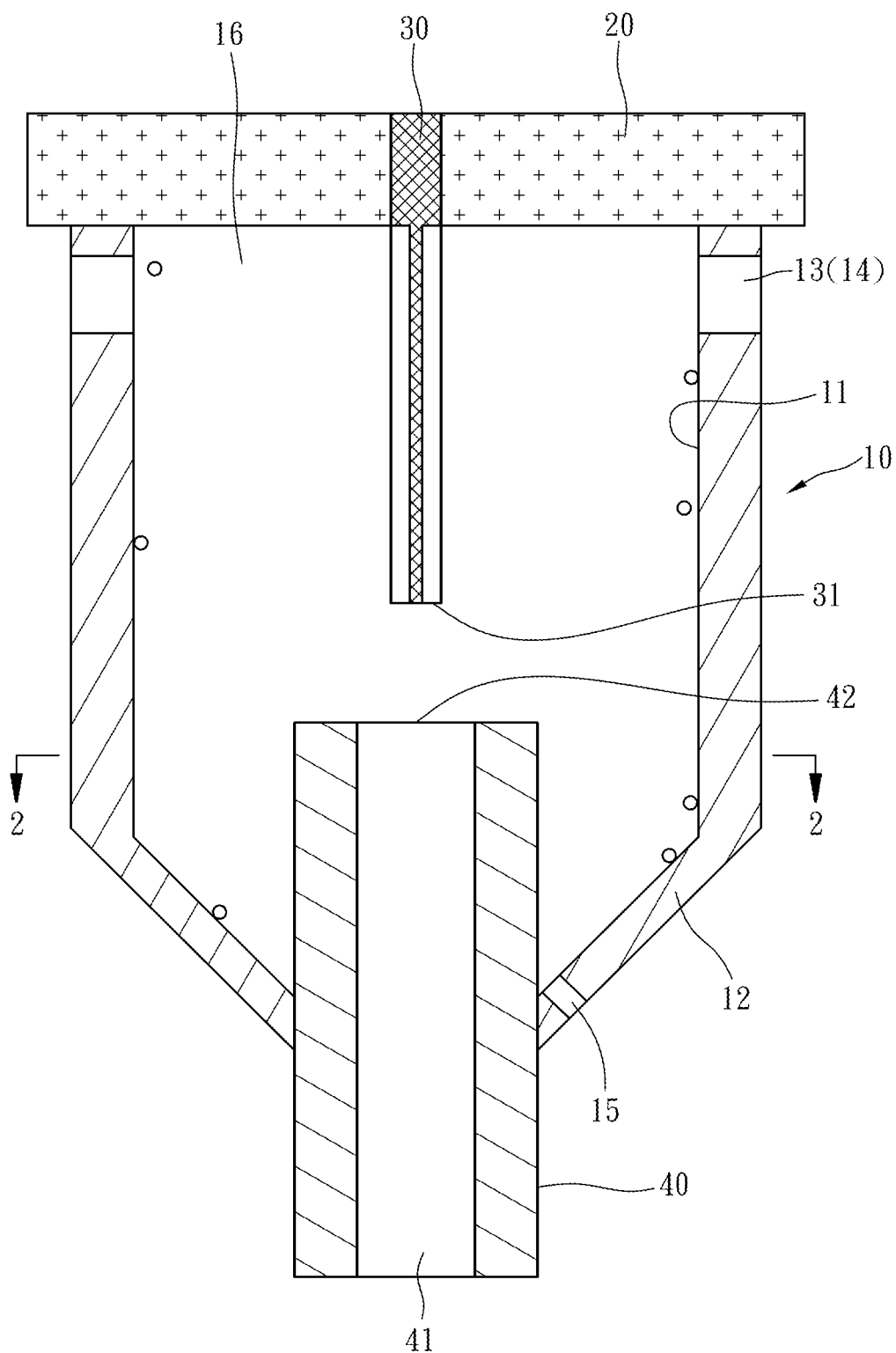
FIG. 1 is a profile of the first embodiment of the present invention.
Figure 2:
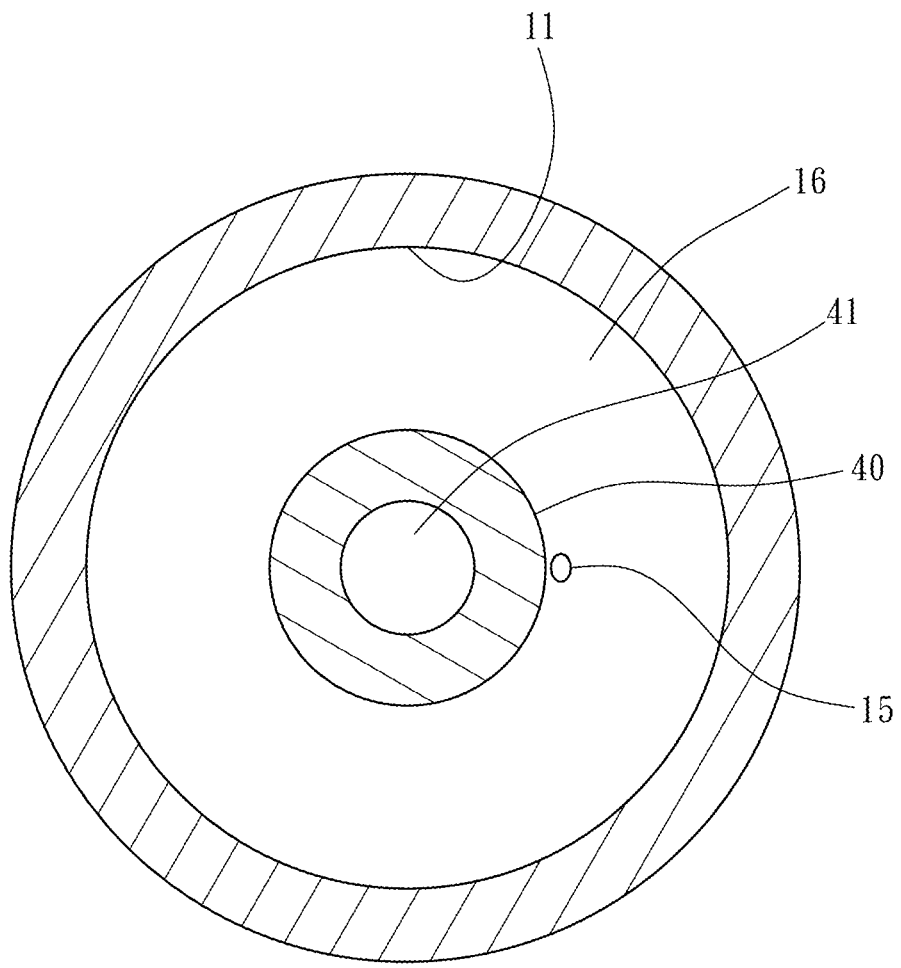
FIG. 2 is a 2-2 sectional view of FIG. 1.

Please refer to FIGS. 1-2 for a semi-dry type electrostatic cyclone sampler of the first embodiment of the present invention, which comprises a cyclone body 10, an insulate element 20, a discharge electrode 30, an air tube 40, an air introducing means, a discharging means, and a flushing means.

The cyclone body 10 has an annular wall 11, a base 12 connecting to a bottom end of the annular wall 11, a gas inlet 13, a water inlet 14, and a water outlet 15. An imaginary axis is defined at the center of the annular wall 11. The water outlet 15 is lower than the water inlet 14. The gas inlet 13 and the water inlet 14 are formed at positions adjacent to a top portion of the annular wall 11. The water outlet 15 is formed at a position adjacent to the bottom of the funnel-shaped base 12. The cyclone body 10 can be made of electrically conductive material, such as stainless steel, aluminum or other conductive metals. Alternatively, the cyclone body 10 can be made of conductive plastics embedded with carbon fibers, graphene or carbon nanotubes. Metal contaminates can be avoided by using the cyclone body of conductive plastics when the semi-dry type electrostatic cyclone sampler is used for metal analysis. Thus more accurate results can be obtained. The numbers of the gas inlet, the water inlet, and the water outlet may each be plural in other possible embodiments The insulate element 20 is disposed at a top of the annular wall 11. The insulate element 20, the annular wall 11, and the base 12 co-define a cyclone chamber 16. The gas inlet 13, the water inlet 14, and the water outlet 15 are communicated with the cyclone chamber 16 respectively. The insulate element 20 can be made of non-electrically conductive material, such as polytetrafluoroethylene.

The discharge electrode 30 is disposed on the insulate element 20 and extends into the cyclone chamber 16 along the imaginary axis. The discharge electrode 30 has a distal end 31. The distal end 31 is lower than the gas inlet 13 and higher than the water outlet 15. The discharge electrode 30 can be made of electrically conductive material.

The air tube 40 is disposed at the base 12 of the cyclone body 10. The air tube 40 defines a passage 41. A top opening 42 is defined at the top end of the air tube 40 to communicate the cyclone chamber 16 with the passage 41. The top opening 42 is lower than the distal end 31 of the discharge electrode 30 but higher than the water outlet 15.

The air introducing means is for introducing particulate-containing air stream into the cyclone chamber 16 through the gas inlet 13 in a way that the air stream spirally flows along the annular wall 11 and generates an air sample which is expelled from the cyclone chamber 16 through the passage 41 of the air tube 40. The air stream may spirally flow along an outer surface of the air tube 40 before leaving the cyclone chamber 16 through the passage 41. In order to introduce the air stream into the cyclone chamber 16, a suction pump or air compressor may be utilized to connect with the gas inlet 13 or the passage 41. In order to guide the air stream to spirally flow along the annular wall 11, the air stream can be introduced into the gas inlet 13 approximately in a tangential direction of the annular wall 11. For example, an angel between the jet immediately exiting the gas inlet 13 and the tangential direction of the annular wall 11 may be smaller than 30 degrees. In other possible embodiments, larger particulates can be removed from the air stream by other dust removal equipment or particulate sorting equipment before the air stream is introduced into the cyclone chamber 16. For example, the air stream introduced into the cyclone chamber 16 may only contain particulates having a diameter smaller than 10 μm (PM10) or 2.5 μm (PM2.5).

The dust removal equipment or the particulate sorting equipment may be, but not limited to, another cyclone, a particle impactor, or a filter cassette.

The discharging means is for applying a high voltage power to the discharge electrode 30 for charging at least a part of the particulates so that the particulates can attach on the annular wall 11. The discharge electrode 30 may electrically connect to a high voltage power supply which provides voltage high enough for the discharge electrode 30 to electrically discharge. The discharge electrode 30 may further have a discharge needle or a discharge edge such that the electrically discharge occurs more easily. When the discharging means is activated, the annular wall 11 may be grounded or have a polarity opposite to the charged particulates such that the particulates can attach on the annular wall 11 more easily.

The flushing means is for introducing water into the cyclone chamber 16 to flush the annular wall 11. For example, the water may be introduced into the cyclone chamber 16 via the water inlet 14 and collects at least a part of the particulates attached on the annular wall 11. In order to introduce the water into the cyclone chamber 16, a water storage and a water pump may connect to the water inlet 14 such that the water can be ejected toward the annular wall 11. The ejecting direction of the water from the water inlet 14 can be approximately the tangential direction of the annular wall 11 such that the ejected water can spirally flush the annular wall 11 for a longer distance. In other possible embodiments, the annular wall 11 may be formed with a plurality of water inlets for the ejected water to sufficiently flush a larger region of the annular wall 11. In other possible embodiments, the water may overflow into the cyclone chamber 16 and flushes the annular wall 11. The particulate-containing water eventually flows to the base 12 of the cyclone body 10 and leaves the cyclone chamber 16 via the water outlet 15. In other possible embodiments, a water pump or other pumping equipment may connect to the water outlet. When the water pumping equipment is activated, an environment with a negative pressure can be generated in the cyclone chamber and hence the water can be sucked into the cyclone chamber from the water inlet and flush the annular wall. Under such circumstances, other water pumping equipment connected with the water inlet is not necessary.

Figure 3:
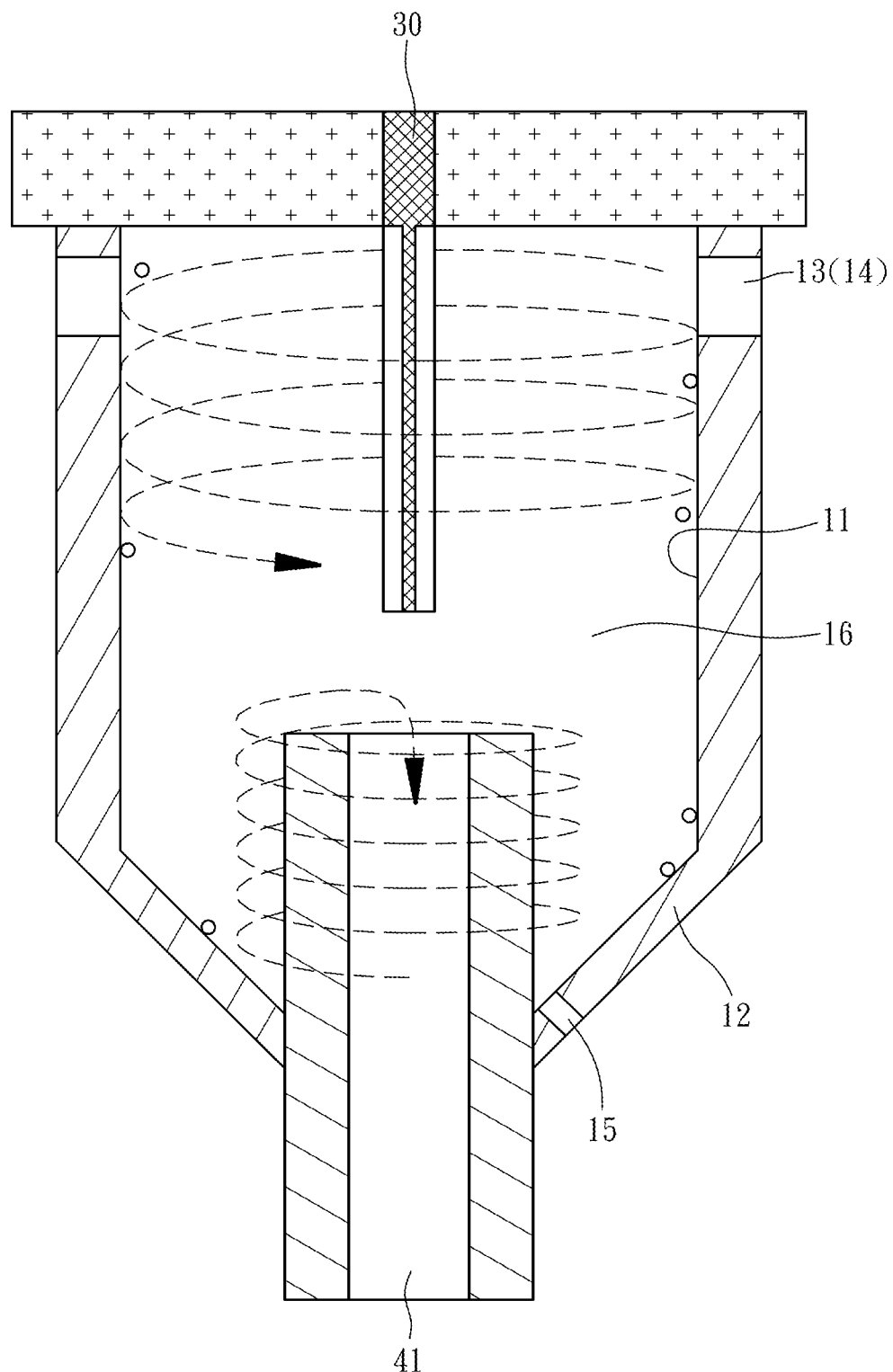
FIG. 3 is a profile of the first embodiment of the present invention, in which the air introducing means and the discharging means are activated simultaneously.

The semi-dry type electrostatic cyclone sampler can be utilized in a manner described hereinafter:

First, referring to FIG. 3, the air introducing means and the discharging means are activated simultaneously. In such instance, particulate-containing air stream enters the cyclone chamber 16 via the gas inlet 13. At least a part of the particulates can attach on the annular wall 11 due to inertia and electrostatic or fall on the base 12. The air stream deprived of at least a part of the particulates then leaves the cyclone chamber 16 via the passage 41 and constitute an air sample. In the case that the air sample is required for later sampling or analysis, the air sample exiting the passage 41 is collected.

The air sample exiting the passage 41 can be collected by, but not limited to, a porous metal denuder sampler (PDS). The PDS has porous metal sheets to collect gas such as $NH_3$, HF, HCl, $HNO_2$, $HNO_3$, and $SO_2$. The analysis method can be done with, but not limited to, an ion chromatography by immersing the porous metal sheet of the PDS into pure water and analyzing ion concentrations of, for example, $NH_4^+$, $F^-$, $Cl^-$, $NO_2^-$, $NO_3^-$, and $SO_4^{2-}$. The ion concentrations are then be converted into gas concentrations. Other analysis method includes, for example, measuring a particular gas concentration by a gas detector.

It is to be mentioned that flushing gas can be introduced into the cyclone chamber 16 prior to the activation of the air introducing means and the discharging means, such that the cyclone chamber 16 can be kept dry in order to obtain a more accurate result of analysis. The flushing gas may be, for example, dry air, nitrogen or inert gas.

Thereafter, deactivating the air introducing means and the discharging means. In other words, the air stream is no longer introduced into the cyclone chamber 16 and the discharge electrode 30 stops discharging.

Figure 4:
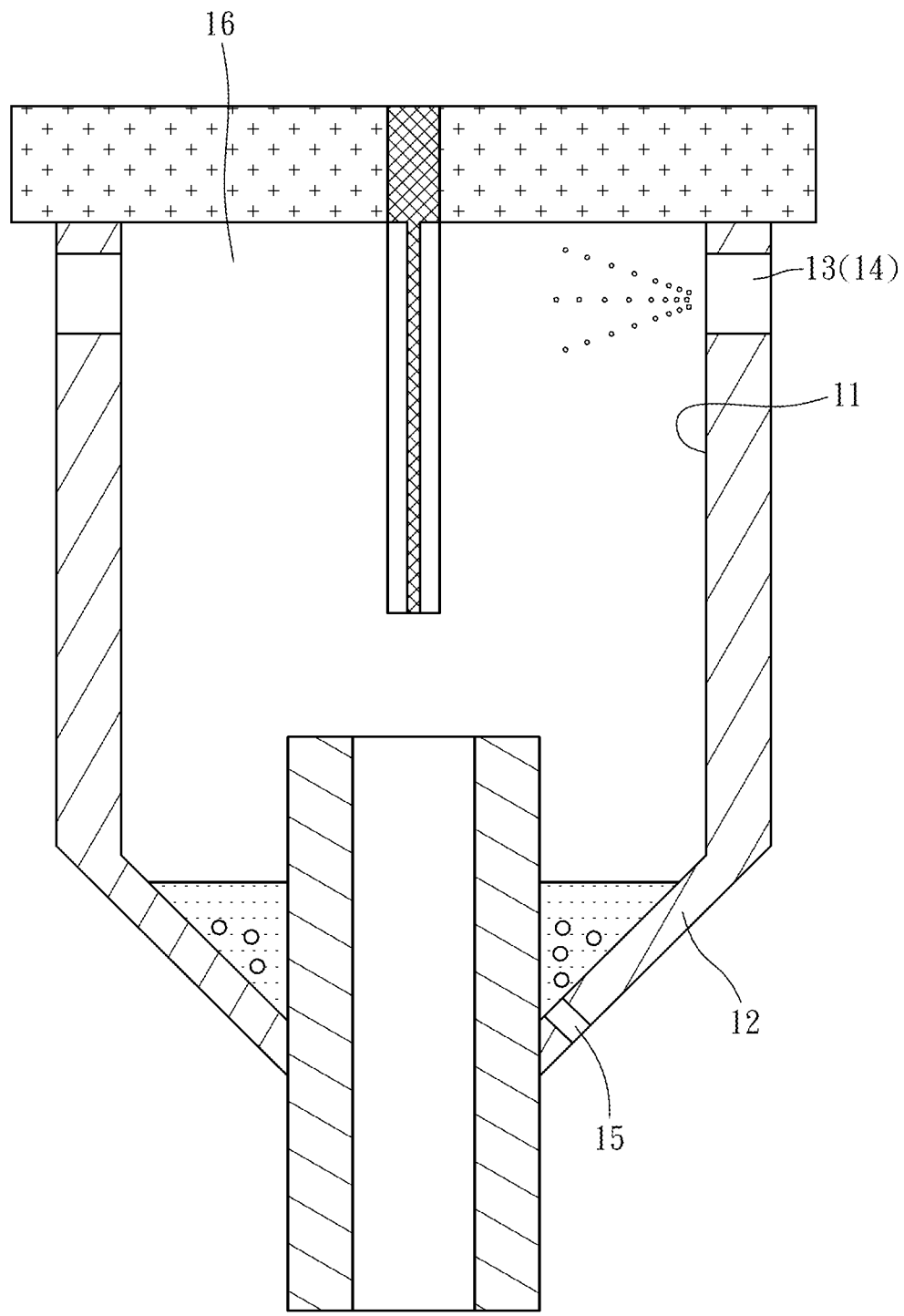
FIG. 4 is a profile of the first embodiment of the present invention, in which the flushing means is activated independently.

Then, referring to FIG. 4, the flushing means is activated to flush the annular wall 11 utilizing flushing liquid such as deionized water or ultrapure water to take at least a part of the particulates away from the annular wall 11. The water then leaves the cyclone chamber 16 via the water outlet 15 located at the bottom of the base 12. In the case that water sample is needed, the water leaving the water outlet 15 is collected and analyzed.

The water sample leaving the water outlet 15 may be collected by, but not limited to, a container. The analysis of the water sample may be, but not limited to, ion concentration analysis or heavy metal ion concentration analysis. The ion concentration analysis may be done by, for example, an ion chromatograph (IC). The heavy metal ion concentration analysis may be done by, for example, an inductively coupled plasma-mass spectrometer (ICP-MS).

Figure 5:
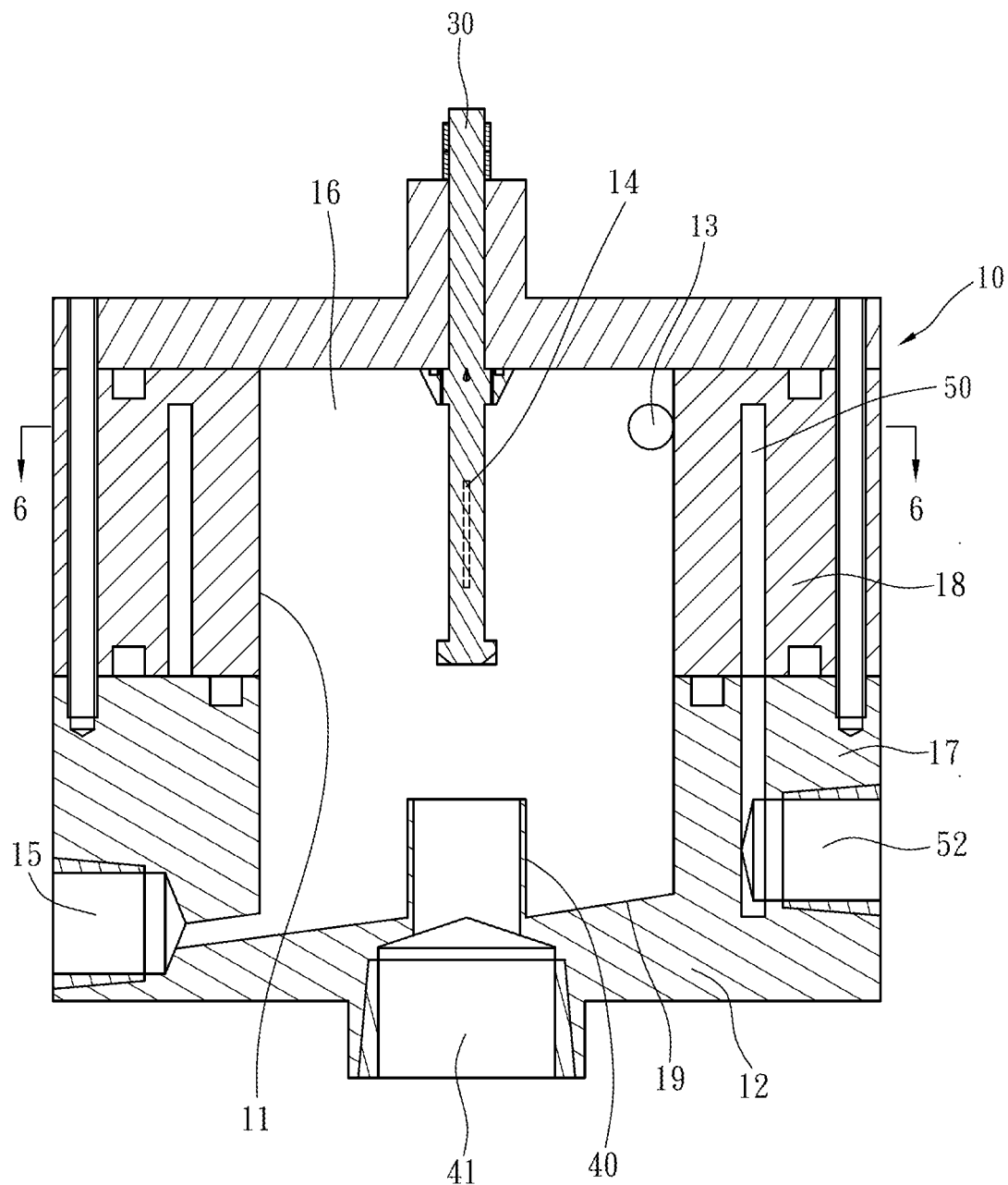
FIG. 5 is a profile of the second embodiment of the present invention.
Figure 6:
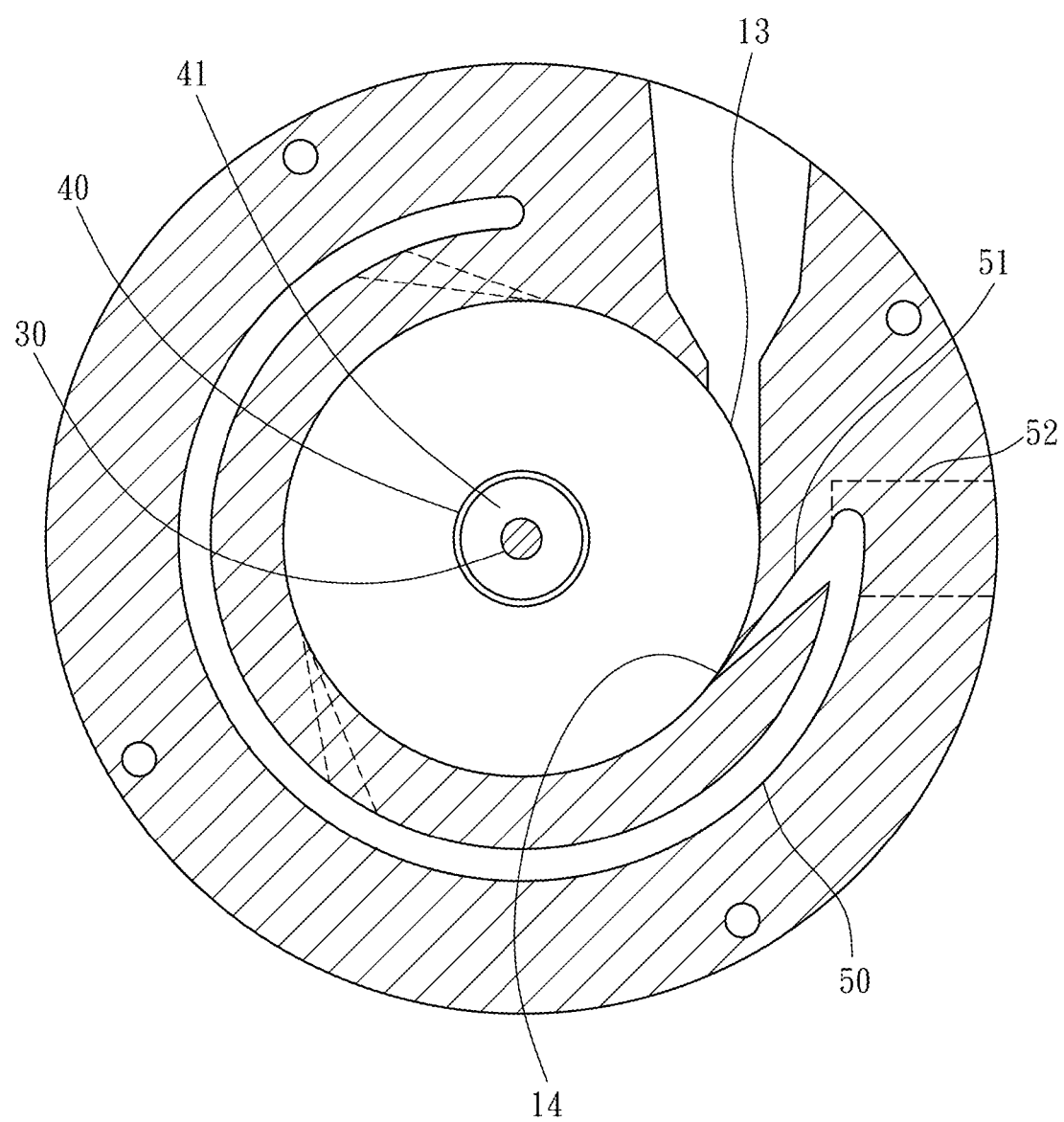
FIG. 6 is a 6-6 sectional view of FIG. 5.

Please refer to FIGS. 5-6 which show the second embodiment of the semi-dry type electrostatic cyclone sampler of the present invention. The structure of the second embodiment is similar to that of the first embodiment. One of the difference between these two embodiments is that the cyclone body 10 of the second embodiment includes a lower portion 17 and an upper portion 18. The cyclone body 10 has a plurality of water inlets 14 locating at different heights on the annular wall 11. The cyclone body 10 further has a water sink 50 located radially outside the annular wall 11 and a plurality of channels 51 corresponding to the water inlets 14 respectively. The channels 51 are communicated with the water sink 50 and the corresponding water inlets 14 respectively. The base 12 of the cyclone body 10 has an inclined surface 19. The water outlet 15 is located at the lowest region of the inclined surface 19. The air tube 40 and the base 12 are formed integrally. A water intake 52 is located radially outside the water sink 50 and connects the water sink 50 with the surrounding such that the water intake 52 is adapted to introduce water into the water sink 50, the channels 51 and further into the cyclone chamber 16 via the water inlets 14.

Several experiments has been taken to verify the effect of the second embodiment. Dry air was introduced into the cyclone chamber 16 prior to the experiments to keep the cyclone chamber 16 dry. The air stream utilized in the experiments was treated in advance such that the air stream only contains particulates smaller than PM2.5. The air stream was introduced into the cyclone chamber 16 at a flow rate of 5 L/min. The air introducing means and the discharging means were activated simultaneously for 24 hours. The air introducing means and the discharging means were then deactivated. Thereafter the flushing means was activated by using 25 ml deionized water, and the water sample exiting the water outlet 15 was collected. The ion concentration in water sample was analyzed by IC. The above mentioned processes were repeated for 4 times. The results are labeled as experimental group in Table 1.

While the above mentioned processes were undertaken, a branch of the same air stream was introduced into a conventional PDS to collect the gas and the particulates in the air stream simultaneously. The PDS has a porous metal sheet for the collection of the gas, and a filter paper for the collection of the particulates. In the present experiment, only the filter paper in the PDS was used and immersed in 30 ml deionized water. Ultrasound wave was applied to the deionized water containing the filter paper to extract the particulates into the water. Then the concentrations of the ions in the water were analyzed by the IC respectively. The so obtained results are labeled as the comparison group in Table 1. It is to be mentioned that the ion ratios of both the experimental group and the comparison group are between 0.8-1.2, indicating that the results of both groups are reliable and representative.

TABLE 1

| | ion concentration in µg/m3 | | | | | | | | |
|---|---|---|---|---|---|---|---|---|---|
| | $Na^+$ | $NH_4^+$ | $K^+$ | $Mg^{2+}$ | $Ca^{2+}$ | $F^-$ | $Cl^-$ | $NO_3^-$ | $SO_4^{2-}$ |
| Experimental group | 0.17 | 2.507 | 0.14 | 0.074 | 0 | 0.03 | 0.17 | 3.15 | 5.21 |
| Comparison group (PDS) | 0.38 | 3.335 | 0.23 | 0 | 0 | 0.02 | 1.31 | 2.92 | 6.86 |
| Experimental group | 0.32 | 2.56 | 0.06 | 0.039 | 0 | 0.01 | 0.44 | 3.28 | 6.47 |
| Comparison group (PDS) | 0.57 | 3.192 | 0.38 | 0.179 | 0.01 | 0.06 | 0.78 | 3.73 | 7.36 |
| Experimental group | 0.37 | 2.533 | 0.43 | 0.284 | 0 | 0.09 | 2.14 | 2.37 | 5.21 |
| Comparison group (PDS) | 0.5 | 2.009 | 0.49 | 0.323 | 0.2 | 0.09 | 2.53 | 2.65 | 6.34 |
| Experimental group | 0.43 | 4.479 | 0.48 | 0.185 | 0.01 | 0.09 | 0.78 | 14.2 | 7.32 |
| Comparison group (PDS) | 0.57 | 5.118 | 0.64 | 0.201 | 0.02 | 0.07 | 1.84 | 12.09 | 8.11 |

The analysis results would have larger deviation if the cyclone chamber 16 was not kept dry, as shown in Table 2. The data of Table 2 were obtained by experiments mostly identical to the above mentioned processes, except that dry air was not introduced into the cyclone chamber 16 before the activation of air introducing means and discharging means. The results indicate that the concentration of $NO_3^-$ in water sample of a wet cyclone chamber (experimental group-wet) is obviously higher than that of the PDS (comparison group).

TABLE 2 ion concentration in μg/m3 using a wet and without hydrophobic agent cyclone chamber.

|  | $Na^+$ | $NH_4^+$ | $K^+$ | $Mg^{2+}$ | $Ca^{2+}$ | $F^-$ | $Cl^-$ | $NO_3^-$ | $SO_4^{2-}$ |
|---|---|---|---|---|---|---|---|---|---|
| Experimental group-wet | 0.07 | 1.89 | 0.11 | 0.23 | 0.01 | 0.02 | 0.09 | 21.05 | 1.94 |
| Comparison group (PDS) | 0.22 | 4.86 | 0.29 | 0.13 | 0 | 0.02 | 0.77 | 5.65 | 7.02 |

In order to increase the accuracy of the sampling, the annular wall may be surface treated to be hydrophobic, such that the annular wall barely has affinity to water. For example, hydrophobic agent may be applied on the surface of the annular wall, and thus water drops introduced by the flushing means can spirally flow and collect particulates more easily without water residual on the annular wall. In other possible embodiments, physical surface treatments can be applied on the annular wall to make the surface denser in order to increase its hydrophobicity.

The next experiment verifies the collecting efficiency of particulates by electrostatic. In this experiment, Diisooctyl sebacate (DOS) particulates were prepared by an atomizer. The air stream contained so prepared DOS particulates and was introduced into a mixing tank in advance to disperse the DOS particulates uniformly in the air stream. Particulates having diameters higher than 2.5 μm were then removed from the air stream by a cyclone. The air stream were then introduced into the gas inlet 13 of the second embodiment of the semi-dry type electrostatic cyclone sampler. Two groups of the experimental data were obtained. The data of the experimental group were obtained under the circumstances that the air introducing means and the discharging means were activated simultaneously. The discharging means applied 1000 V to the discharge electrode 30. The data of the comparison group were obtained under the circumstances that the air introducing means was activated without applying voltage to the discharge electrode 30. The air sample leaving the air tube 40 was introduced into a scanning mobility particle sizer (SMPS) to measure DOS particulate concentration, which is hereinafter referred to as outflow particulate concentration ($N_{out}$). In addition the inflow particulate concentration, hereinafter ($N_{in}$), was also measured by the SMPS before the air steam was introduced into the gas inlet 13. The collecting efficiency (η) of DOS particulates is obtained by the following equation:

$$\eta(\%) = \left(1 - \frac{N_{out}}{N_{in}}\right) \times 100$$

Figure 7:
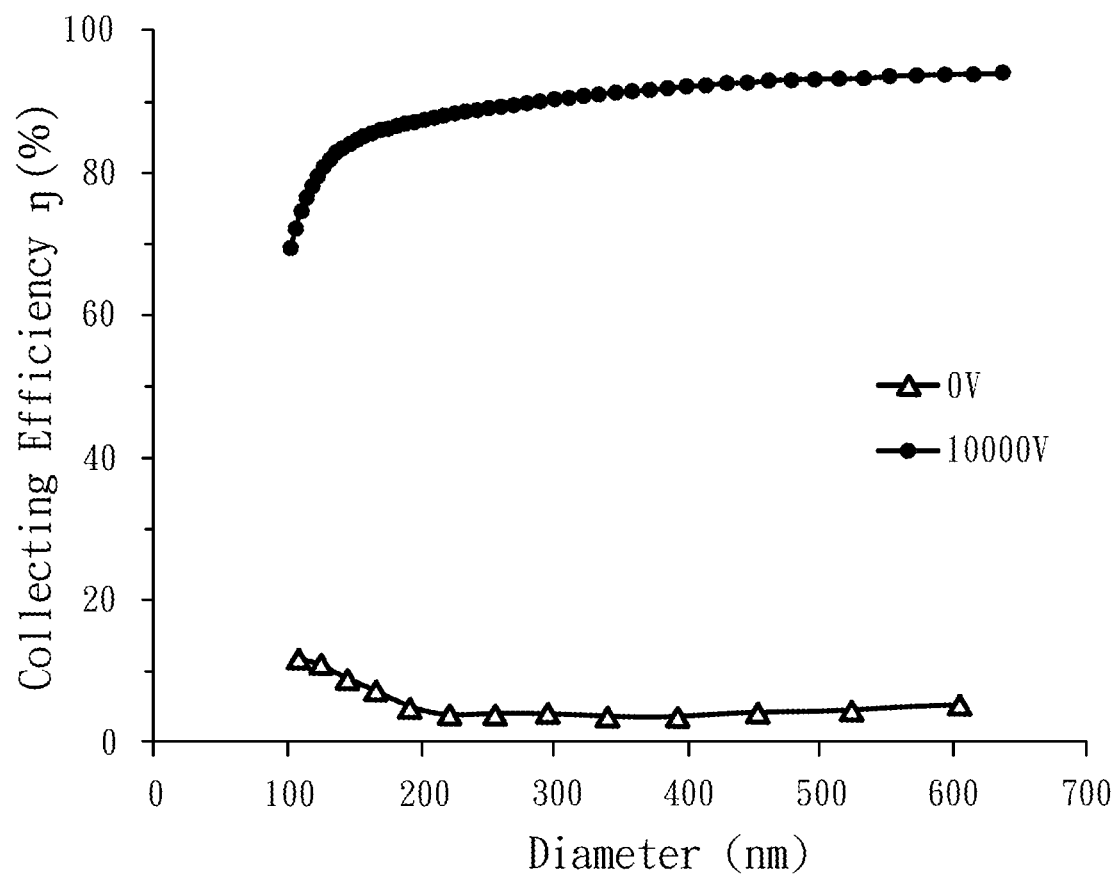
FIG. 7 is a diagram showing the relationship of the collecting efficiency versus diameter of the particulates using the second embodiment of the present invention.

The result is shown in FIG. 7. The collecting efficiency (η) of DOS particulates with diameter between 100-600 nm when applying 1000 V high voltage power is 57% higher than that without applying voltage.

Figure 8:
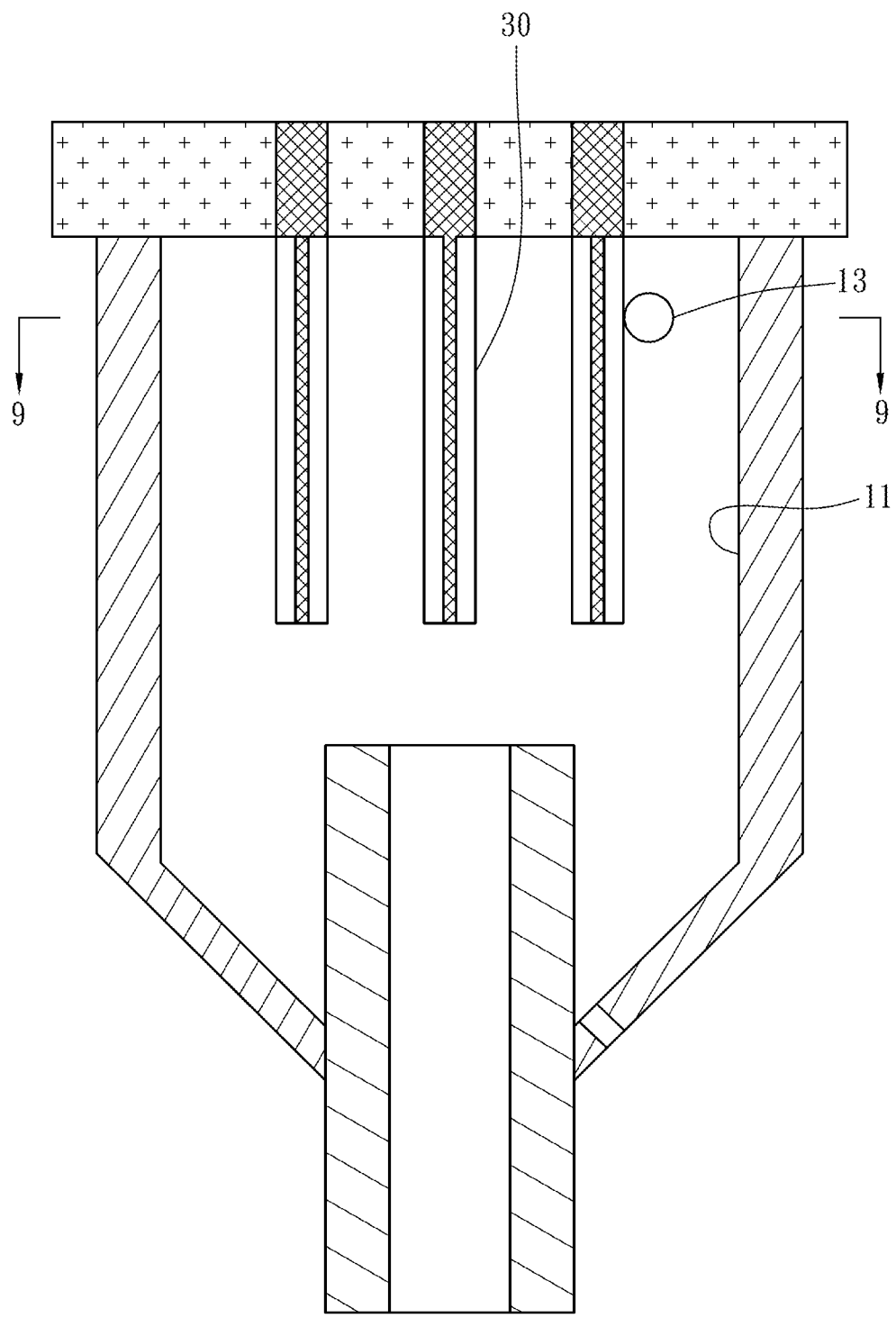
FIG. 8 is a profile of the third embodiment of the present invention.
Figure 9:
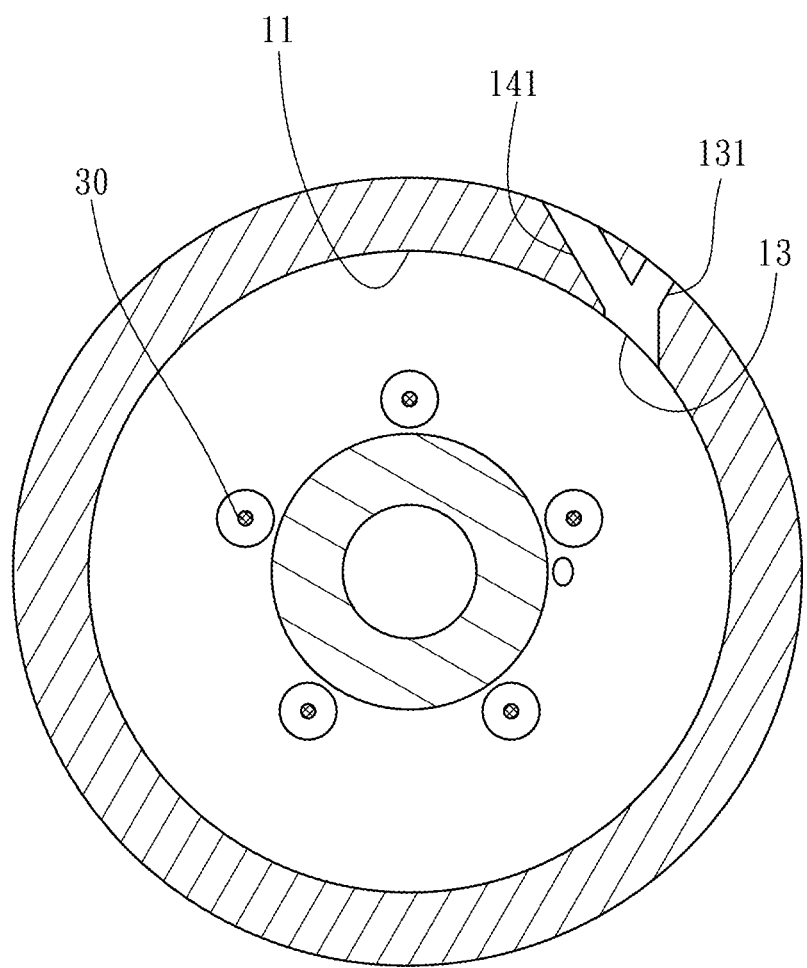
FIG. 9 is a 9-9 sectional view of FIG. 8.

Please refer to FIGS. 8-9 which show the third embodiment of the present invention. In the third embodiment, there are a plurality of discharge electrodes 30 in which the geometric center of the discharge electrodes 30 as a whole is overlapped with the imaginary axis of the annular wall 11. There is no water inlet on the annular wall 11. The gas inlet 13 communicates with a gas entry channel 131 and a water entry channel 141. When the air introducing means is activated, air stream is introduced into the cyclone chamber 16 via the gas entry channel 131 and the gas inlet 13. When the flushing means is activated, water is introduced into the cyclone chamber 16 via the water entry channel 141 and then the gas inlet 13. A water storage and a water pump or other equipment providing water pressure can be connected to the water entry channel 141 to eject water toward the annular wall 11 via the gas inlet 13.

Figure 10:
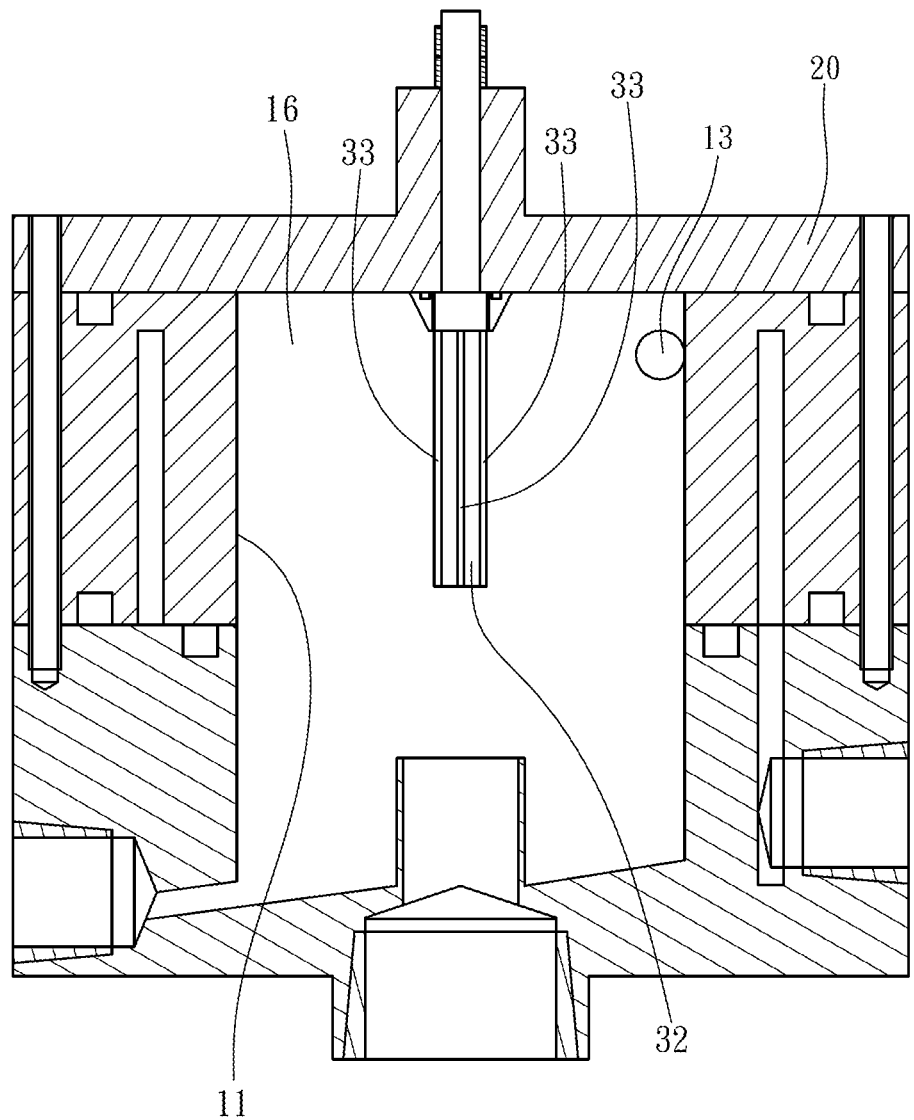
FIG. 10 is a profile of the fourth embodiment of the present invention, in which the discharge electrodes and the insulated cylinder are intactly shown.

Please refer to FIG. 10 which shows the fourth embodiment of the present invention. The structure of the fourth embodiment is similar to that of the second embodiment, except that the arrangement of the discharge electrodes is different. In the fourth embodiment, an insulated cylinder 32 is disposed at the center of the insulate element 20 and extends into the cyclone chamber 16. The insulated cylinder 32 may be made of non-electrically conductive material such as polytetrafluoroethylene. The insulated cylinder 32 may be solid or hollow. Several electrode wires 33 are disposed on the outer surface of the insulated cylinder 32 as discharge electrodes at equal intervals. The electrode wires 33 extends closely on the outer surface of the insulated cylinder 32 along the axial direction of the cyclone chamber 16. The electrode wires 33 are electrically connect to a high voltage power supply and are adapted for electrically discharge when the discharging means is activated. The particulates collecting efficiency (η) of the fourth embodiment was measured. In this experiment, sodium chloride particulates were used as test particulates. The air stream containing sodium chloride particulates was introduced into the gas inlet 13 of the fourth embodiment at a flow rate of 3 L/min after removing particulates larger than 2.5 μm. The shortest distance between the electrode wires and the annular wall 11 was set at 0.45 cm. The voltage of the electrode wires 33 was kept at 5300 V. The result shows that the average collecting efficiency is larger than 90%.

With the aforementioned design, when the air introducing means and the discharging means are activated simultaneously, particulates in the air stream can attach on the annular wall by effects of inertia or electrostatic. The air sample exiting the air tube can also be collected and analyzed. The flushing means can collect the particulates away from the annular wall. The water sample leaving the water outlet contains so collected particulates and is adapted for later sampling and analysis. Hence, the objective of collecting gas and/or water sample individually is achieved.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What we claim is:

1. A semi-dry type electrostatic cyclone sampler comprising:
    a cyclone body having an annular wall, a base connecting to a bottom end of the annular wall, at least one gas inlet, and at least one water outlet;
    an insulate element disposed at a top end of the annular wall co-defining a cyclone chamber with the annular wall and the base of the cyclone body; the gas inlet and the water outlet both communicating with the cyclone chamber;

at least one discharge electrode disposed on the insulate element and extending into the cyclone chamber; the discharge electrode having a distal end lower than the gas inlet and higher than the water outlet;

an air tube disposed at the base of the cyclone body defining a passage; a top end of the air tube being defined as a top opening communicating with the cyclone chamber and the passage;

the top opening of the air tube being lower than the distal end of the discharge electrode and higher than the water outlet;

an air introducing means for introducing a particulate-containing air stream into the cyclone chamber through the gas inlet in a way that the air stream spirally flows along the annular wall and generates an air sample which is expelled from the cyclone chamber through the passage;

a discharging means for applying a high voltage power to the discharge electrode to charge at least a part of the particulates in a way that the charged particulates can attach on the annular wall; and a flushing means for introducing water into the cyclone chamber to flush the annular wall, collect at least a part of the particulates attached on the annular wall and thus form a particulates-containing water sample;

wherein the water outlet is adapted for the particulates-containing water sample to leave the cyclone chamber;

wherein, when the discharging means is activated, the air introducing means is activated simultaneously; when the flushing means is activated, the discharging means is deactivated.

2. The semi-dry type electrostatic cyclone sampler of claim 1, wherein the cyclone body further has at least one water inlet communicating with the cyclone chamber, the water outlet is lower than the water inlet, the flushing means is adapted for introducing water into the cyclone chamber via the water inlet.

3. The semi-dry type electrostatic cyclone sampler of claim 2, wherein the cyclone body further has a plurality of water inlets disposing on the annular wall at different heights.

4. The semi-dry type electrostatic cyclone sampler of claim 2, wherein the cyclone body defines a water sink and at least one channel corresponding to the at least one water inlet therein, the channel communicates with the water sink and the corresponding water inlet, the water sink locates outside the annular wall in a radial direction.

5. The semi-dry type electrostatic cyclone sampler of claim 1, wherein the base of the cyclone body is funnel-shaped, the water outlet locates adjacent to a bottom end of the base of the funnel-shaped cyclone body.

6. The semi-dry type electrostatic cyclone sampler of claim 1, further comprising an insulated cylinder disposed on the insulate element and extending into the cyclone chamber, the at least one discharge electrode being an electrode wire attaching to the surface of the insulated cylinder and extending along an axial direction of the cyclone chamber.

7. The semi-dry type electrostatic cyclone sampler of claim 1, wherein the surface of the annular wall is hydrophobic.

8. A gas and water sampling method using the semi-dry type electrostatic cyclone sampler of claim 1 including the following steps:

(1) activating the air introducing means and the discharging means simultaneously, collecting and analyzing the air sample leaving the passage;

(2) deactivating the air introducing means and the discharging means; and (3) activating the flushing means, collecting and analyzing the particulate-containing water sample leaving the water outlet.

9. A water sampling method using the semi-dry type electrostatic cyclone sampler of claim 1 including the following steps:

(1) activating the air introducing means and the discharging means simultaneous;

(2) deactivating the air introducing means and the discharging means; and (3) activating the flushing means, collecting and analyzing the particulate-containing water sample leaving the water outlet.

10. The water sampling method of claim 9, wherein a flushing gas is introduced into the cyclone chamber before the step (1).

* * * * *